(12) United States Patent
Pedersen et al.

(10) Patent No.: US 9,289,559 B2
(45) Date of Patent: Mar. 22, 2016

(54) INJECTION DEVICE INCORPORATING DOSE MONITORING

(75) Inventors: Bennie Peder Smiszek Pedersen, Haslev (DK); Michael Ejstrup Hansen, Morud (DK); Lars Peter Klitmose, Gentofte (DK); Kim Ejholm Hansen, Alleroed (DK); Dennis B. Hansen, Copenhagen OE (DK)

(73) Assignee: Novo Nordisk A/S, Bagsvaerd (DK)

( * ) Notice: Subject to any disclaimer, the term of this patent is extended or adjusted under 35 U.S.C. 154(b) by 156 days.

(21) Appl. No.: 14/110,601

(22) PCT Filed: Apr. 11, 2012

(86) PCT No.: PCT/EP2012/056598
§ 371 (c)(1),
(2), (4) Date: Nov. 26, 2013

(87) PCT Pub. No.: WO2012/140097
PCT Pub. Date: Oct. 18, 2012

(65) Prior Publication Data
US 2014/0074041 A1    Mar. 13, 2014

Related U.S. Application Data

(60) Provisional application No. 61/476,535, filed on Apr. 18, 2011.

(30) Foreign Application Priority Data

Apr. 11, 2011    (EP) ..................................... 11161912

(51) Int. Cl.
*A61M 5/315*    (2006.01)
*A61M 5/20*    (2006.01)
(Continued)

(52) U.S. Cl.
CPC .............. *A61M 5/31585* (2013.01); *A61M 5/20* (2013.01); *A61M 5/24* (2013.01); *A61M 5/31541* (2013.01);
(Continued)

(58) Field of Classification Search
CPC ............. A61M 2005/2407; A61M 2005/3126; A61M 5/20; A61M 5/24; A61M 5/31541; A61M 5/31543; A61M 5/31553; A61M 5/31578; A61M 5/31583; A61M 5/31585; A61M 5/31593
See application file for complete search history.

(56) References Cited

U.S. PATENT DOCUMENTS 4,787,645 A    11/1988    Ohbayashi et al.
7,695,456 B2    4/2010    Langley et al.
(Continued)

FOREIGN PATENT DOCUMENTS

DE    102004063650    7/2006
WO    0195959 A1    12/2001
(Continued)

*Primary Examiner* — Quynh-Nhu H Vu
(74) *Attorney, Agent, or Firm* — Wesley Nicolas

(57) ABSTRACT

The present invention relates to an electronically assisted injection device adapted to inject doses of a drug from a held cartridge. The injection device may include a first rotational sensor (40) coupled to a driver (6) for sensing a dose setting and a second rotational sensor (50) coupled to a dosing member (8) for sensing an expelled dose. A third axial sensor (60) provides information relating to the axial position of the driver (6). A control circuit is adapted to determine the end of dosed state based on data from the first, the second and the third sensors (40, 50, 60). The injection device may also include an arrangement for determining fluid ingress into the interior of the injection device. The arrangement includes an electrically non-conductive surface portion (63) disposed on a first component (6) and an electrode assembly (62a, 62b, 62c) disposed on a second component (80) wherein the first component (6) and the second component (80) moves relative to each other during operation.

11 Claims, 10 Drawing Sheets

(51) Int. Cl.
  *A61M 5/24* (2006.01)
  *A61M 5/31* (2006.01)
(52) U.S. Cl.
  CPC ....... *A61M 5/31543* (2013.01); *A61M 5/31553* (2013.01); *A61M 5/31578* (2013.01); *A61M 5/31593* (2013.01); *A61M 5/31583* (2013.01); *A61M 2005/2407* (2013.01); *A61M 2005/3126* (2013.01); *A61M 2205/15* (2013.01)

(56) References Cited

U.S. PATENT DOCUMENTS

| | | | |
|---|---|---|---|
| 8,298,171 | B2 * | 10/2012 | Ishikawa et al. ................ 604/65 |
| 2002/0198483 | A1 | 12/2002 | Wariar et al. |
| 2003/0009131 | A1 | 1/2003 | Van Antwerp et al. |
| 2009/0131875 | A1 | 5/2009 | Green |
| 2009/0318865 | A1 * | 12/2009 | Moller et al. ................ 604/135 |
| 2009/0326459 | A1 * | 12/2009 | Shipway et al. ............... 604/155 |
| 2010/0238038 | A1 * | 9/2010 | Kohlbrenner et al. ........ 340/635 |
| 2011/0009821 | A1 * | 1/2011 | Jespersen et al. ............. 604/135 |

FOREIGN PATENT DOCUMENTS

| | | |
|---|---|---|
| WO | 02064196 | 8/2002 |
| WO | 02/092153 | 11/2002 |
| WO | 2008/021462 A2 | 2/2008 |
| WO | 2008/037801 | 4/2008 |
| WO | 2008116766 A1 | 10/2008 |
| WO | 2010/052275 A2 | 5/2010 |
| WO | 2010/142598 A2 | 12/2010 |

* cited by examiner

Dosage tube Gray code

| Index | G4 | G3 | G2 | G1 | Wake-up |
|---|---|---|---|---|---|
| 0 | 1 | 1 | 1 | 0 | 0 |
| 1 | 1 | 1 | 0 | 0 | 1 |
| 2 | 1 | 1 | 0 | 1 | 0 |
| 3 | 1 | 0 | 0 | 1 | 1 |
| 4 | 1 | 0 | 1 | 1 | 0 |
| 5 | 0 | 0 | 1 | 1 | 1 |
| 6 | 0 | 1 | 1 | 1 | 0 |
| 7 | 0 | 1 | 1 | 0 | 1 |

Fig.12a

Locking nut Gray code

| Index | G4 | G3 | G2 | G1 |
|---|---|---|---|---|
| 0 | 1 | 1 | 1 | 0 |
| 1 | 1 | 1 | 0 | 0 |
| 2 | 1 | 1 | 0 | 1 |
| 3 | 1 | 0 | 0 | 1 |
| 4 | 1 | 0 | 1 | 1 |
| 5 | 0 | 0 | 1 | 1 |
| 6 | 0 | 1 | 1 | 1 |
| 7 | 0 | 1 | 1 | 0 |

Fig.12b

INJECTION DEVICE INCORPORATING DOSE MONITORING

CROSS-REFERENCE TO RELATED APPLICATIONS

This application is a 35 U.S.C. §371 National Stage application of International Application PCT/EP2012/056598 (WO 2012/140097), filed Apr. 11, 2012, which claimed priority of European Patent Application 11161912.8, filed Apr. 11, 2011; this application claims priority under 35 U.S.C. §119 of U.S. Provisional Application 61/476,535; filed Apr. 18, 2011.

The present invention relates to medical injection devices adapted for injecting apportioned doses of a drug. More specifically, the invention relates to medical injection devices incorporating a dose setting mechanism and an injection mechanism and incorporating means for electronically monitoring movements of components of the device.

The invention offers improvements with respect to the reliability in detecting positional information associated with the movable components of the device.

BACKGROUND OF THE INVENTION

In the disclosure of the present invention reference is mostly made to the treatment of diabetes by injection or infusion of insulin, however, this is only a preferred use of the present invention.

In order to permit a patient to administer a proper dose, various mechanical injection devices have been proposed such as the devices shown in WO 01/95959 and WO 2008/116766. Some devices incorporates additional electric circuitry for measuring and displaying the size of a dose which is being set during a dose setting procedure or which is being administered during an injection procedure. Examples of such devices are shown in WO 02/092153 and in WO 02/064196.

In terms of safety, it is generally preferred that both movements during dose setting and during dose injection are being monitored. However, it remains a challenge to design a system which provides adequate reliability and robustness and which at the same time enables the device to be manufactured in an inexpensive way.

WO 2008/037801 includes disclosure of an injection device wherein separate sensor systems are respectively associated with a dose setting mechanism and an injection mechanism. Such sensor configuration may offer additional reliability having regard to the monitoring of the components which moves during dose setting and during injection. However, the described choice of sensor circuitry may prove difficult to calibrate and hence may prove expensive to manufacture.

Another problem with some existing injection devices is that potential liquid ingress into the interior of the injection device, such as fluid drug leaking from a held cartridge, may render the operation of the device inoperable or faulty.

The reference US 2003/0009131 A1 deals with measures for detecting fluid that leaks outside normal fluid paths in a fluid delivery system. The references includes disclosure of fluid detectors arranged on or near the reservoir which containing the fluid to be delivered into an individual's body. A related system is described in U.S. Pat. No. 4,787,645.

Having regard to the above-identified prior art devices, It is an object of the invention to provide an electronically assisted injection device in which the monitoring of movements of the mechanical components during operation of the device is accurately and safely performed.

It is a further object of the invention to provide an electronically assisted injection device that may be manufactured in an inexpensive way.

It is a further object of the invention to provide an electronically assisted injection device in which it is possible to control movements of the piston rod in a more accurate manner than in similar prior art devices and to utilize this for improving the reliability of the electronic monitoring of positional information relating to particular components of the injection device.

It is a further object of the invention to provide an electronically assisted injection device which provides improvements in the detection of potential fluid ingress into interior parts of the injection device.

SUMMARY OF THE INVENTION

In a first aspect the present invention relates to an injection device for setting and expelling set doses of a drug from a drug-filled cartridge of the kind comprising an outlet and a slideably arranged piston which is driveable in a distal direction to expel the drug through the outlet. The injection device further comprises a) a housing, b) a piston rod adapted to cooperate with the piston of the cartridge to cause a set dose to be expelled, c) a driver coupled to the piston rod, the driver being rotated during dose setting away from an initial position to effect the adjustment of the effective length of the piston rod and the driver, d) a dosing member mounted rotatably movable but axially fixed in the housing, the dosing member being prevented from rotating during dose setting and allowed to rotate during dose delivery, the dosing member controlling the distal movement of the piston rod during dose injection.

Further, the injection device comprises e) a first sensor adapted to provide data indicative of the rotational position of the driver relative to the housing, f) a second sensor adapted to provide data indicative of the rotational position of the dosing member relative to the housing, g) a third sensor adapted to provide data indicative of the axial position of the driver relative to the housing, h) a control circuit coupled to the first, second and third sensors, the control circuit being adapted to determine the rotational positions of the driver and the dosing member and adapted to determine an amount of a set dose and/or an amount of an expelled dose based on the rotational position of the driver relative to the rotational position of the dosing member. The control circuit is adapted to determine the state wherein the driver is in the initial position relative to the dosing member based on data from the first sensor, data from the second sensor and data from the third sensor.

The initial position may correspond to a so-called end of dose state, i.e. the condition that the driver assumes after a complete expelling of a previously set dose. In some embodiments, the third sensor is of the type that exclusively provides one or more state changes when the driver is a pre-defined length from the end of dose state. By combining information from the third sensor and the information relating to the relative rotation between the driver and the dosing member, the end of dose state may be reliably detected by means of a relatively simple sensor configuration. Hence, the typical requirements relating to tolerances associated with components used for sensing the mechanical movements of the system becomes critical. Furthermore, due to the above sensor configuration, the first and second sensors need not be provided as absolute sensors thereby simplifying the design. This allows for the device to be manufactured in a particular economical way. During operation, in case that one of the first and second sensors experience a sensor error of the kind which may be deemed recoverable, the well-defined mechanical state between the driver and dosing member around the end of dose state may be utilized to reinitialize the sensor system.

In the present context the term 'injection device' should be interpreted to mean a device which is suitable for injecting a drug, such as a liquid drug, into a human or animal body. The injection device is preferably of the kind being suitable for performing repetitive self injection of drug, e.g. insulin for persons having diabetes, or growth hormone. The injection device may be in the form of an injection pen, i.e. of a kind having an elongated shape similar to that of an ordinary pen. Such injection device generally is characterized in that the device part which is intended to rest against an injection site is only held against the skin of the patient during injection of the drug, such as for a duration of less than 1 minute for the complete expelling of a previously set dose.

As mentioned above, the drug is preferably a liquid drug suitable for injection into a human or animal body, e.g. subcutaneously or intravenously. Alternatively, the drug may be a dry drug which has to be reconstituted prior to injection.

The housing is a part of the injection device which at least substantially encloses the remaining parts of the injection device. Thus, the housing generally defines an outer boundary of the injection device that holds a mechanism for setting and expelling set doses. In addition, the housing may define a housing component that separates a cartridge section from a mechanism section that is situated proximally relative to the cartridge. The said housing component may include an opening through which the piston rod protrudes. The housing may be substantially closed to seal off the housing relative to exterior effects such as moisture and fluid ingress.

The injection device may define a longitudinal axis which is defined by the piston rod, or in case the piston rod is provided as a flexible piston rod, the part of the piston rod that in situation of use is situated in the vicinity of a piston of a held cartridge.

The driver of the device provides a telescopic engagement to the piston rod. In some embodiments, the driver forms a dosage tube. Such dosage tube may be threadedly connected to the piston rod by means of an external thread or by means of an internal thread. In alternative embodiments, a telescopic engagement between the driver and the piston rod is provided by means of ratchet mechanism such as by means of ratchet teeth providing a one-way lengthening of the assembly formed by the driver and the piston rod.

In some embodiments, the dosing member comprises a first thread while the driver comprises a second thread engaged with the first thread of the rotatable dosing member. In such an embodiment the driver moves in a proximal direction during dose setting as it rotates through the engagement with the dosing member away from an initial rotational position relative to the dosing member. During dose delivery the driver performs a non-rotational displacement in the distal direction while the dosing member rotates, The above discussed initial rotational position may be defined by corresponding features on the driver and the dosing member so as to provide a rotational stop where blocking features on the driver and the dosing member each define geometric features that extends in the axial direction. Alternatively, the rotational stop is defined by a discontinuation in the threaded engagement between the driver and the dosing member. A similar arrangement may be arranged to define a maximum dose stop for the driver relative to the dosing member.

The described embodiments enables a particular accurate and well defined end of dose position of the driver, the end of dose position corresponding to the abovementioned initial rotational position of the driver. Such accurate relative positioning between the driver and the dosing member may be utilized for adjusting the outputs of the first and the second sensors relative to each other, i.e. performing a mechanical synchronization between the first and the second sensor.

The driver may be rotatable relative to the dosing member through an angular movement exceeding one revolution.

In some embodiments, the driver is rotatable relative to the dosing member in discrete rotational steps. Such step-wise movement may be provided by means of a click mechanism.

In some embodiments the first and/or the second sensor is/are adapted to provide rotational position data corresponding to N discrete rotational steps distributed evenly over degrees of rotation. Exemplary values of N may be 16, 20, 24, 30 or 32.

The rotational resolution of the first and/or the second sensor may correspond to the incremental rotational steps provided by the click mechanism. In other embodiments, the resolution of the first and/or the second sensor may be 2 or 3 times the resolution of the click mechanism.

In some embodiments the first and/or the second sensor is/are adapted to provide unique rotational position data for each respective rotational positions of the respective one of the driver and the dosing member over a range of n rotational positions, wherein n is a division of N and N/n is a natural number. In one form the parameter n is selected as 8.

In some embodiments, the first and/or the second sensor is/are provided as rotary digital encoders such as rotary Gray code sensor(s).

The third sensor and the control circuit may be adapted to determine whether or not the driver is in the range of p rotational positions from said initial rotational position of the driver relative to the dosing member. In an embodiment where n is 8, example parameter values of p may be selected as a number in the range from 0 to 6.

The control circuit may be configured to determine the amount of a set dose and/or the amount of an expelled dose based on the number of complete and fractional relative rotations between the driver and the dosing member.

The initial rotational position of the driver (corresponding to the end of dose position) relative to the dosing member may be determined by means of the third sensor and by means of the differential rotational position between the driver and the dosing member as determined by the first sensor and the second sensor.

The third sensor may be adapted to provide an output signal when the driver is within p rotational positions from said initial rotational position of the driver relative to the dosing member.

Also, the third sensor may be adapted to provide one or more state changes only when the driver is within p rotational positions from said initial rotational position of the driver relative to the dosing member as the dosing member and the driver moves towards the initial rotational position.

In some embodiments, the first and/or the second sensor may comprise one or more code tracks arranged as circumferential band(s) on a cylindrical surface. The code tracks may be provided on an interior cylindrical surface where sensors arranged internally relative to the code tracks are arranged to read the code tracks. Alternatively, the code tracks may be provided on an external cylindrical surface where sensors are arranged externally to the code tracks.

In other embodiments, the first and/or the second sensor may comprise rotational planar code tracks that may be arranged transverse to a longitudinal axis of the device.

In a second aspect the present invention relates to a injection device for setting and expelling set doses of a drug from a drug-filled cartridge of the type that comprises an outlet and a slideably arranged piston which is driveable in a distal direction to expel the drug through the outlet. The injection device according to the second aspect comprises:

a) a housing comprising a housing component forming an opening, and b) a dose setting and injection mechanism operable to set a dose and to expel a set dose, the dose setting and injection mechanism comprising a piston rod adapted to cooperate with the piston of a held cartridge to cause a set dose to be expelled where the piston rod is adapted to protrude through the opening of the housing component. The dose setting and injection mechanism defines a first component and a second component that moves relative to each other during operation of the dose setting and injection mechanism, An electrically non-conductive surface portion is disposed on the first component and an electrode assembly comprising at least a first electrode and a second electrode is disposed on the second component. The electrode assembly and the electrically non-conductive surface portion are configured to move relatively and next to each other during operation of the dose setting and injection mechanism. A control circuit is coupled to the electrode assembly. The control circuit is configured to sense an electrical characteristic associated with the electrode assembly to determine the presence of a fluid on the electrically non-conductive surface portion.

The above determination of the presence of a fluid, such as a fluid ingress of a leaking cartridge is performed on the basis of a component that moves during operation of the device. As the components moves back and forth relative to other structures of the device a fluid film is likely to be formed on one of the components and this effect is utilized to transport eventual fluid towards the detection system. Hence, the above fluid determination principle enables more rapid fluid detection enabling countermeasures to be rapidly performed.

It is to be noted that the term "component" should be interpreted to encompass both a single entity as well as an assembly formed by a plurality of members.

The said first component of the device may be a component that moves relative to the housing component during operation of the dose setting and injection mechanism. In other embodiments the second component moves relative to the housing component. In still other embodiments both the first and the second component move relative to the housing component.

In some embodiments the first component slides back and forth relative to the second component as the dose setting and injection mechanism is operated. Examples include devices where the first component is defined by the piston rod. Other examples include a component coupled to the piston rod, such as a driver engaging the piston rod, where the component moves as the piston rod moves during the dose setting operation and/or during the dose expelling operation.

In different embodiments, the first component performs a linear movement relative to the second component, a rotational movement relative to the second component or a combined linear and rotational movement relative to the second component.

In some embodiments the electrodes of the electrode assembly are contact arms adapted to engage the electrically non-conductive surface portion at least for particular relative positions between the first component and the second component. In such embodiments, the contact arms are adapted to slide relative to electrically non-conductive surface portion of the first component. In other embodiments some or all of the electrodes of the electrode assembly are spaced slightly away from the electrically non-conductive surface portion, however with only a small distance so that minor liquid quantities may be formed between the electrically non-conductive surface portion and the electrodes.

In order to provide a fast responding detection of fluid ingress into the housing, the component(s) that move relative to the housing and that may carry the electrically non-conductive surface portion or the electrode assembly may be selected as a component that slides back and forth in the vicinity of the opening of the housing component. In some embodiments the component may be one that, at least for particular relative positions between the first and the second component, is positioned no further than 15-25 mm from the opening of the housing component.

Depending on the technology used for sensing the electrical characteristic that is sensed between the first and second electrodes and optionally via the electrical non-conductive surface portion may include one or more of the electrical characteristics of a voltage, an impedance or a capacitance. For example, the control circuit may be adapted to sense whether or not a short circuit between the electrodes has occurred. Should a fluid be present on the non-conductive surface portion, an electrical characteristic between the electrodes will be modified compared to the normal situation where no fluid will be present. This will be detected by the control circuit and the device is configured to generate a warning. The injection device may be configured to determine whether a determined fluid ingress should provide only a warning or whether some or all of the electronic features of the device should be rendered inoperable, either temporarily or permanently.

In some embodiments, the injection device includes a dose sensor arrangement adapted to provide data associated with the setting of a dose and/or the expelling of a dose. In addition, a control circuit is coupled to the sensor arrangement, the control circuit being configured to determine an amount of a set dose and/or an amount of an expelled dose. In case a liquid ingress into the housing is determined a warning may be generated to indicate that the determined amount of a set dose or the amount of an expelled dose will not be reliable.

In some embodiments, the individual sensors of the sensor arrangement that provides data associated with the setting of a dose and/or the expelling of a dose may be additionally be used to determine the presence of a fluid between the individual sensors or on an electrically non-conductive surface portion of a cooperating component.

In some embodiments the first and the second electrodes of the electrode assembly may be arranged with a slight separation in the order of 0.2 mm to 5 mm, such as within the range 0.5 mm to 3 mm. Although some embodiments described above include two galvanically separate electrodes other configurations may include three or more galvanically separate electrodes that are disposed along different areas of the electrically non-conductive surface portion.

The electrically non-conductive surface portion disposed on the first component may be an integral part of component being made fully of an electrically insulating material. Alternatively, the first component may be made of a metal that may be electrically conductive by where surface portions may be formed such as by attachment of a further non-conductive component or such as by forming an electrically non-conductive protection layer on top of the electrically conductive material.

In some embodiments, as disclosed herein elsewhere, the electrode assembly that is utilized for determining the presence of fluid on the electrically non-conductive surface portion may additionally be used for detecting the end-of-dose state of the dose setting and injection mechanism. As discussed in connection with the embodiments relating to the first aspect of the invention such end-of-dose detection may incorporate a driver coupled to the piston rod. Also, any other feature mentioned in relation to the first aspect may be combined with the features discussed in relation to the second aspect.

Further features that in further embodiments may combine with an injection device according to the first aspect and/or according to the second aspect may include one or more of the following features.

In some embodiments, the injection device may comprise:
a housing,
a dose setting mechanism being operable to set a desired dose, the dose setting mechanism comprising a rotatable dose knob, operation of the dose setting mechanism causing energy to be stored in a spring member,
an injection mechanism comprising a piston rod adapted to cooperate with a piston positioned in a cartridge containing a drug to be delivered in order to cause a set dose to be delivered from the cartridge via the injection device, the injection mechanism being driven by releasing energy previously stored in the spring member during dose setting,
a driver being axially movable in a proximal direction relatively to the housing during dose setting and being axially movable in a distal direction relatively to the housing during injection of a set dose, and
retaining means arranged to prevent axial movement of the driver in a distal direction relatively to the housing during dose setting.

The dose setting mechanism is the part of the injection device which is used for setting a desired dose. It may advantageously comprise a part which can be manipulated by an operator and one or more parts which ensure(s) that when an operator manipulates the relevant part, then the injection device is set in such manner that when the injection mechanism is subsequently operated, the desired dose is actually injected by the injection device. The operator operates the dose setting mechanism by rotating a rotatable dose knob.

The injection mechanism is the part of the injection device which is used for injecting a desired dose once is has been set by means of the dose setting mechanism. The injection mechanism comprises a piston rod, and the piston rod is adapted to cooperate with a piston positioned in a cartridge. This typically takes place by causing the piston rod to move in an axial direction in the injection device during injection of a previously set dose. The piston rod is typically arranged in the injection device in such a manner that it abuts the piston arranged in the cartridge, and axial movement of the piston rod will therefore cause corresponding axial movement of the piston in the cartridge. Thereby drug is expelled from the cartridge and injected by the injection device. The injection mechanism preferably comprises a part which can be operated by an operator, e.g. an injection button or a release mechanism, e.g. for releasing energy which was previously stored in the spring member during dose setting.

The driver is axially movable in a proximal direction relatively to the housing during dose setting, and it is axially movable in a distal direction relatively to the housing during injection of a set dose. In the present context the term 'distal direction' should be interpreted to mean a direction substantially along a longitudinal axis of the injection device, and towards an end being adapted to receive an injection needle. Similarly, in the present context the term 'proximal direction' should be interpreted to mean a direction substantially along the longitudinal axis of the injection device, and substantially opposite to the distal direction, i.e. away from the end being adapted to receive an injection needle. The proximal direction is preferably in a direction towards the position of the rotatable dose knob.

The driver is preferably connected to the rotatable dose knob in such a manner that rotating the dose knob causes the driver to move axially in a proximal direction. Furthermore, the driver is preferably connected to the spring member in such a manner that moving the driver axially in a proximal direction causes energy to be stored in the spring member, and in such a manner that releasing energy stored in the spring member causes axial movement of the driver in a distal direction. Finally, the driver is preferably connected to the piston rod in such a manner that axial movement of the driver in a distal direction causes the piston rod to cooperate with the piston to cause a set dose to be delivered.

The retaining means is arranged to prevent axial movement of the driver in a distal direction relatively to the housing during injection of a set dose. In the case that the driver is connected to the spring member and the piston rod as described above, the retaining means, thus, prevents the spring member from releasing the stored energy and cause the piston rod to cooperate with the piston to inject drug during dose setting. Thus, it is prevented that drug is accidentally spilled, and it is ensured that a correct dose is being set. Controlling this by axially retaining the driver rather than locking the piston rod directly has the following advantage. When a cartridge is empty and therefore has to be replaced, it is necessary to return the piston rod to an initial position corresponding to a full cartridge. In the case that axial movement of the piston rod in a distal direction during dose setting is prevented by directly locking the piston rod, e.g. by means of a locking item or a dosing member, it may be difficult to return the piston rod during replacement of the cartridge. This is particularly the case when the piston rod and the locking item/dosing member are engaged in such a manner that they tend to jam. However, according to the present invention axial movement of the piston rod in a distal direction is prevented by axially retaining the driver, and the risk of jamming the piston rod during replacement of the cartridge is thereby minimised, since the piston rod is allowed to return freely to the initial position.

The retaining means may be a dosing member being axially fixed relatively to the housing, and the dosing member may be adapted to be rotationally locked relatively to the housing during dose setting, and it may be adapted to be able to perform rotational movement relatively to the housing during injection of a set dose. According to this embodiment, when the dosing member is rotationally locked relatively to the housing, it axially retains the driver, i.e. it prevents the driver from performing axial movements in a distal direction. However, when the dosing member is allowed to perform rotational movement relatively to the housing it allows the driver to move axially in a distal direction.

The dosing member and the driver may be connected via mating threads formed on the driver and the dosing member, respectively. According to this embodiment the driver can be moved axially in a proximal direction by rotating the driver, thereby allowing it to climb the threaded connection between the dosing member and the driver. However, the threaded connection prevents that the driver is pushed in a purely axial movement in a distal direction as long as the dosing member is not allowed to rotate relatively to the housing. When the dosing member is subsequently allowed to rotate, the driver is allowed to move axially in a distal direction while causing the dosing member to rotate.

The injection device may further comprise a locking item being movable between a locking position in which it prevents the dosing member from rotating relatively to the housing, and an unlocking position in which the dosing member is allowed to rotate relatively to the housing. According to this embodiment the locking item is in its locking position during dose setting and in its unlocking position during injection of a set dose. Mating teeth may be formed on the dosing member and the locking item, respectively, and these mating teeth may engage when the locking item is in the locking position. When the locking item is moved into its unlocking position, the mating teeth are, in this case, moved out of engagement, thereby allowing mutual rotational movement between the dosing member and the locking item.

The locking item may be moved from the locking position to the unlocking position in response to operation of the injection mechanism. According to this embodiment, the locking item is automatically moved into the unlocking position when a user operates the injection mechanism. Thereby the injection device is automatically shifted from a state where a dose can be set into a state where a dose can be injected when the user operates the injection mechanism. Thereby the user only has to perform a single operation in order to cause a set dose to be injected, and the injection device is thereby very easy to operate.

As an alternative to a dosing member, the retaining means may, e.g., be or comprise a key and groove connection, one or more braking elements, one or more slidable locking elements, and/or any other means being suitable for axially retaining the driver as described above during dose setting.

The driver may be prevented from performing rotational movements relatively to the housing during injection of a set dose. According to this embodiment the driver moves in a purely axial manner relatively to the housing during injection of a set dose. This provides a very simple movement pattern, and the risk that the injection device jams during injection of a set dose is minimised.

The driver and the piston rod may be connected via mating threads formed on the driver and the piston rod, respectively. According to this embodiment, the driver is preferably moved along this threaded connection during dose setting. During injection the piston rod is preferably moved along the driver in an axial movement.

In a preferred embodiment the driver is threadedly connected to the piston rod as well as to a dosing member. For instance, the driver may comprise an inner thread arranged to engage an outer thread of the piston rod and an outer thread arranged to engage an inner thread of the dosing member. According to this embodiment, the piston rod, the driver and the dosing member are preferably arranged relatively to each other in such a manner that at least part of the driver surrounds at least part of the piston rod, and at least part of the dosing member surrounds at least part of the driver. As an alternative, the piston rod may be hollow, and the driver may, in this case comprise an outer thread arranged to engage an inner thread of the hollow piston rod.

The injection device may further comprise means for preventing rotational movement of the piston rod during dose setting. The means for preventing rotational movement of the piston rod may comprise a key and groove connection between the piston rod and a member being fixed relatively to the housing. Such a key and groove connection prevents the piston rod from rotating relatively to the housing, but relative axial movement is possible. The member is fixed relatively to the housing during normal operation, i.e. at least when a cartridge is inserted in the housing. However, the member may advantageously be fixed to the housing in such a manner that it is released, e.g. allowing rotational movements of the member relatively to the housing, during change of cartridge. Such an arrangement would allow the piston rod to be moved back during change of cartridge. This will be explained in more detail below with reference to the drawings.

Alternatively, the means for preventing rotational movement of the piston rod may comprise an additional thread connection provided between the piston rod and a member being fixed relatively to the housing. The remarks set forth above relating to the member being fixed to the housing are equally applicable here. The additional thread connection preferably has a pitch being directed in a direction which is opposite to the direction of the first thread. According to this embodiment the first thread connection between the dosing member and the piston rod and the additional thread connection between the member and the piston rod in combination prevent rotational movement of the piston rod during dose setting, and thereby prevent axial movement of the piston rod during dose setting.

The driver may further be threadedly connected to the dose knob via a second thread connection. According to this embodiment the driver is preferably rotated along the second thread connection during setting of a dose.

As an alternative, the driver may be connected to the dose knob via a key and groove connection. In this case the driver is simply rotated along with the dose knob during dose setting, and the dose knob and the driver are allowed to perform mutual axial movements.

The operation of the dose setting mechanism causes energy to be stored in a spring member, and the injection mechanism is driven by releasing energy previously stored in said spring member during dose setting. The spring member may, e.g., comprise a spring, such as a compressible spring or a torsion spring, or it may be or comprise any other suitable means capable of storing mechanical energy and subsequently releasing the stored energy. Such an injection device is very easy to use for persons having poor dexterity or low finger strength, e.g. elderly people or children, because only a relatively small force needs to be applied by the user in order to inject a set dose, since the necessary mechanical work is carried out by the spring member. Furthermore, in injection devices where the injection is performed by releasing energy previously stored in a spring member, the piston rod is normally moved during injection by applying a pushing force to the piston rod in a substantially axial direction.

The injection device may further comprise a release mechanism for releasing energy stored in the spring member, thereby causing a set dose to be injected. The release mechanism may, e.g., comprise a release button which the user operates. The release mechanism is preferably axially movable, and it may be operable by a user pressing a release button in a substantially axial direction. In some embodiments the release button may be integral with the dose knob.

BRIEF DESCRIPTION OF THE DRAWINGS

The invention will now be described in further detail with reference to the accompanying drawings in which FIGS. 12a and 12b represent tables of sensor values of the sensor systems of FIG. 11a and FIG. 11b respectively.

DETAILED DESCRIPTION OF THE DRAWINGS

FIGS. 1 through 5 illustrate an injection device 1 comprising a dose setting mechanism for setting a dose of a drug and a dose injection mechanism for injecting previously set doses. In accordance with the present invention, such device mechanism is suitable for use with a sensing system described in connection with FIGS. 6 through 12. The device shown in FIGS. 1-5 generally corresponds to the embodiment shown in FIGS. 11-15 of WO 2008/116766, this document being incorporated herein by reference.

The dose setting and injection mechanism included in injection device 1 is adapted to operate in two mechanical operational modes, respectively designated Dose Setting Mode and Dosing Mode. In Dose Setting Mode, dose setting may be performed by dialling up and down a manually operable dose setting member. In this mode, the piston rod of the device is held stationary so that no dose will be expelled. In Dosing Mode, altering an already set dose is prevented while the expelling of an already set dose can be performed. The mechanism may include a mechanical transition zone between the Dose Setting Mode and the Dosing Mode, the transition zone being designated Safe Mode. Safe Mode is a zone ensuring that neither dose setting nor dose expelling can be performed.

Figure 1A:
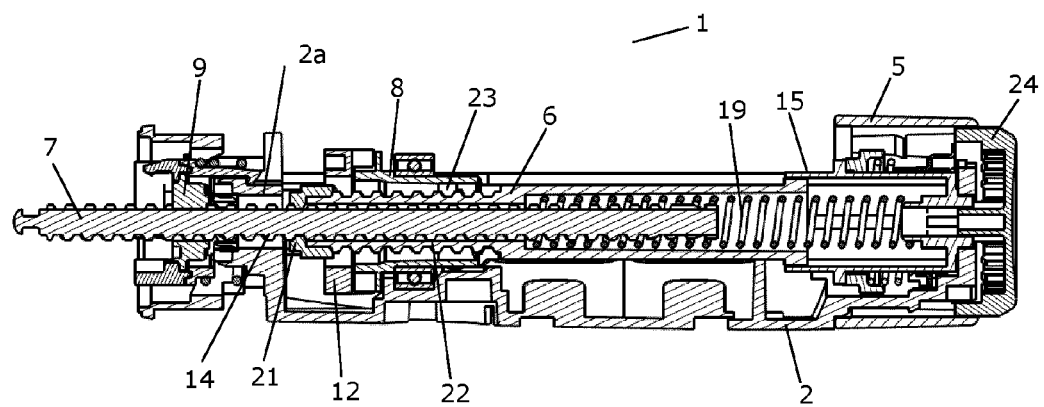
FIGS. 1a and 1b shows cross sectional and top views of an mechanical parts of an injection device suitable for use with an electronic sensing system according to the present invention, the injection device being in a position where it is ready to set a dose.
Figure 1B:
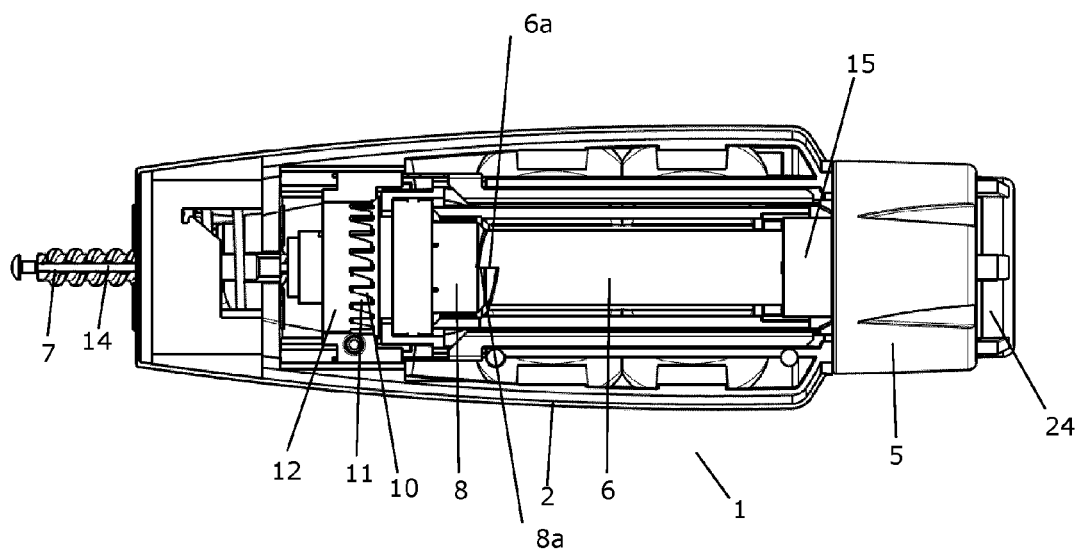

In FIG. 1, the injection device 1 is shown in a position where it is ready for setting a dose. In FIG. 1a the injection device 1 is shown in a cross sectional view, and in FIG. 1b the injection device 1 is shown in a top view with some of the parts omitted for the sake of clarity and in order to show parts arranged in the interior of the injection device and to illustrate their operation.

The injection device 1 of FIG. 1 (FIGS. 1a and 1b) includes a housing component 2 and comprises a driver which in the following will be referred to as a dosage tube 6 and a dosing member which in the following will be referred to as a locking nut 8. The device 1 further comprises a piston rod 7 which is adapted to protrude in the distal direction through an opening 2a in housing component 2 to cooperate with a piston of a cartridge (not shown). In this embodiment the dosage tube 6 is threadedly connected to the piston rod 7 via inner thread 21 formed on the dosage tube 6 and a corresponding outer thread 14 formed on the piston rod 7. The dosage tube 6 is further provided with an outer thread 22. The dosage tube 6 and the locking nut 8 are threadedly connected via the outer thread 22 of the dosage tube 6 and inner thread 23 formed on the locking nut 8. The outer thread 22 of the dosage tube 6 covers only part of the length of the dosage tube 6. Thereby the distance which the dosage tube 6 is allowed to travel relatively to the locking nut 8 is limited, and the ends of the outer thread 22 of the dosage tube 6 define end positions of the relative movement between the dosage tube 6 and the locking nut 8. Accordingly, it is not possible to set a dose which is smaller than a dose corresponding to one end position, and it is not possible to set a dose which is larger than a dose corresponding to the other end position. The minimum dose setting may be defined by rotational stop surfaces 6a and 8a respectively being formed by dosage tube 6 and locking nut 8. In the shown embodiment, a corresponding rotational stop (not visible in FIGS. 1-5) is associated with the dosage tube 6 and locking nut 8 for defining the maximum allowable dose setting. A set of teeth 10 formed on the locking nut 8 and a set of teeth 11 formed on the locking item 12 engage as can be seen in FIG. 1b. The locking item 12 is rotationally locked to the housing component 2, and the engagement of the teeth 10, 11 thereby prevents the locking nut 8 from rotating. By means of the teeth 10,11 the locking nut is designed to be locked rotationally relative to the housing in a number of pre-defined rest-positions, i.e when the teeth 10 of the locking nut 8 engages the teeth 11 of the locking item 12.

In the injection device 1, the dose setting member forms a dose knob 5. When it is desired to set a dose the dose knob 5 is rotated. The dose knob 5 is rotationally locked to injection button 24 via a first spline connection. The injection button 24 is rotationally locked to dose setting item 15 via a second spline connection. The dose setting item 15 is rotationally locked to the dosage tube 6 via a third spline connection. Accordingly, when the dose knob 5 is rotated, the dosage tube 6 is rotated along. Due to the threaded connection between the dosage tube 6 and the locking nut 8, and because the locking nut 8 is prevented from rotating, due to the engagement between teeth 10, 11, the dosage tube 6 is thereby moved axially in a proximal direction relative to the locking nut 8, and in a spiralling movement. Simultaneously, the dosage tube 6 climbs along the piston rod 7 which remains fixed relative to the housing component 2.

In the shown embodiment, the injection device includes a spring device in the form of a helical compression spring 19 arranged internally between the dosage tuve 6 and the dose setting item 15. During dose setting, the axial movement of the dosage tube 6 causes compressible spring 19 to be compressed, i.e. energy is stored in the compressible spring 19. The distance travelled by the dosage tube 6 corresponds to the dose being set.

Figure 5:
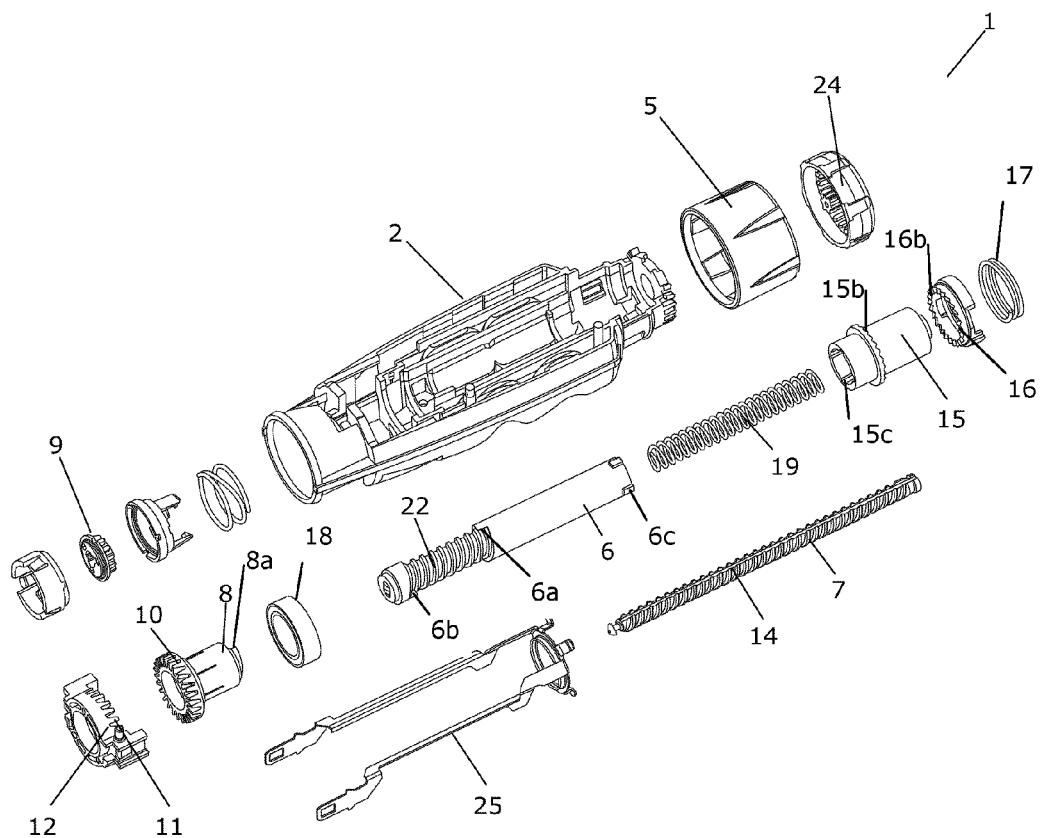
FIG. 5 is an exploded view of selected parts of the injection device of FIGS. 1-4.

An initially set dose may be dialled down fully or partly by reversing the direction of rotation of dose knob 5. Such dialling down may be performed all the way to the zero dose dial position to thereby return the dosage tube 6 to the initial relative rotational position between the dosage tube 6 and the locking nut 8. The injection device 1 may include an indexing mechanism whereby the dose knob 5 is configured to move in discrete rotational steps corresponding to the desired dose increments, i.e. providing a number of pre-defined rest-positions, (i.e. locking positions) between locking nut 8 relative to the housing 2. Referring to FIG. 5, such an indexing mechanism may be provided as a spring biased click-mechanism including a knurled ring surface 15b on dose setting item 15 which engages a corresponding knurled surface 16b on a ring shaped surface defined by indexing member 16. Click spring 17 provides a biasing force for biasing the knurled ring surface on dose setting against the corresponding knurled surface on ring-shaped indexing member 15. In the shown embodiment, the dose knob 5 is adapted to rotate in 24 rotational steps during each revolution that the dose knob 5 undergoes during dose setting, i.e. corresponding to 24 dose increments. The minimum and maximum limit stops defined between dosage tube 6 and locking nut 8 are decisive for the relative rotational and axial movement between these components and may be defined to a total of say 80 or 100 dose increments.

In some embodiments, the force originating from the compressible spring 19, when compressed, may tend to automatically dial down an initially set dose. However, the inclusion of an indexing mechanism may prevent this by adequately designing the indexing mechanism to provide reluctance against self-returning of the dose knob 5.

Figure 2A:
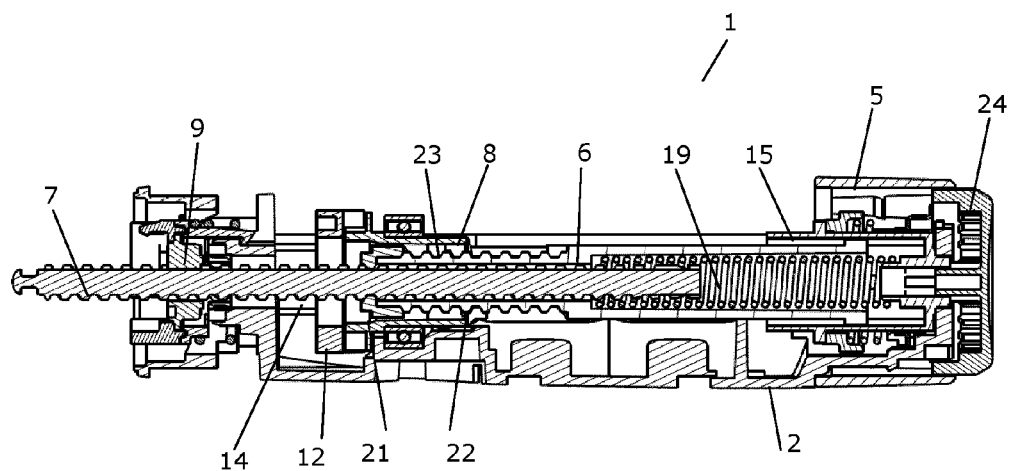
FIGS. 2a and 2b shows similar views of the injection device of FIG. 1 in a position where a dose has been set.
Figure 2B:
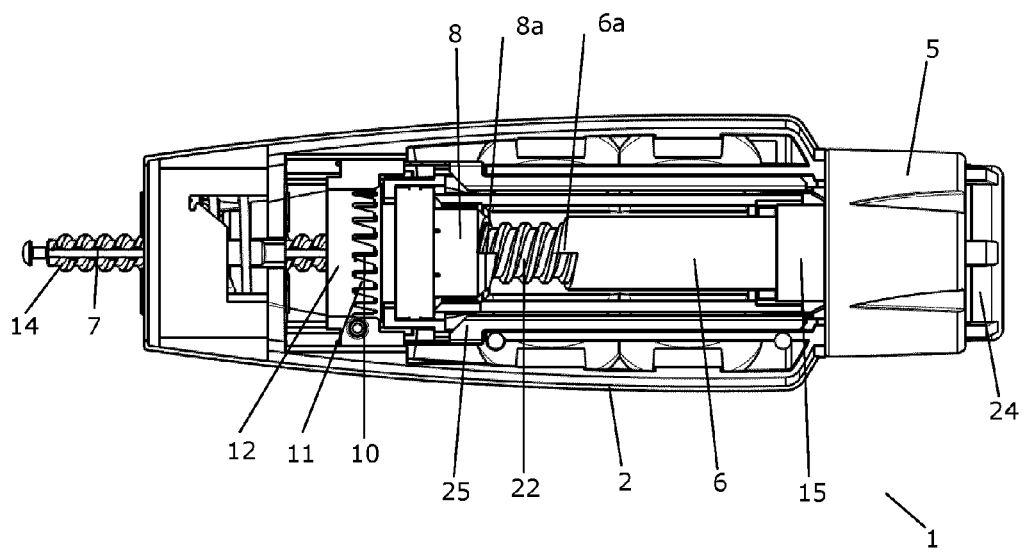

FIGS. 2a and 2b show the injection device 1 of FIGS. 1a and 1b in a position where a dose has been set. In FIG. 2a the injection device 1 is shown in a cross sectional view, and in FIG. 2b the injection device 1 is shown in a top view with some of the parts omitted for the sake of clarity, similar to FIG. 1 b.

Comparing FIGS. 1a+1b and FIGS. 2a+2b it is clear that the dosage tube 6 has been moved in a proximal direction and that the compressible spring 19 has been compressed. In FIG. 2a it can be seen that the dosage tube 6 is arranged in such a manner that the inner thread 23 of the locking nut 8 is positioned very close to one of the ends of the outer thread 22 of the dosage tube 6. Thus, the dose which has been set is very close to the maximum settable dose. In FIG. 2b the outer thread 22 of the dosage tube 6 is visible.

In FIG. 2b it can be seen that the teeth 10 formed on the locking nut 8 and the teeth 11 formed on the locking item 12 are still engaged, i.e. the locking nut 8 is still prevented from rotating relatively to the hosing 2. Thus, the dosage tube 6 is retained in the position shown in FIG. 2.

When it is desired to inject the set dose, the injection button 24 is pushed in a distal direction, i.e. towards the housing component 2. The injection button 24 is connected to the locking item 12 via connecting part 25. Accordingly, pushing the injection button 24 causes the locking item 12 to move along in a distal direction, thereby moving the teeth 10, 11 out of engagement, allowing the locking nut 8 to rotate. The injection button 24 is configured in such a manner that it automatically returns to its initial distal position when external pressure acting on the injection button 24 is released. In the shown embodiment this is obtained by means of click spring 17.

The locking nut 8 may be mounted relative to the housing by means of a ball bearing or similar to provide a low-frictional rotation of the locking nut 8 during dosing.

Figure 3A:
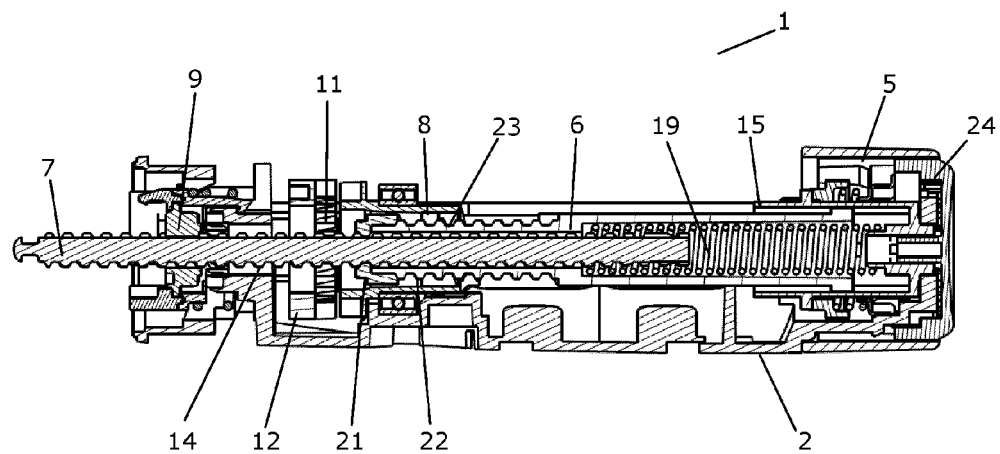
FIGS. 3a and 3b shows similar views of the injection device of FIGS. 1 and 2 in a position where a dose has been set and the injection button has been pushed.
Figure 3B:
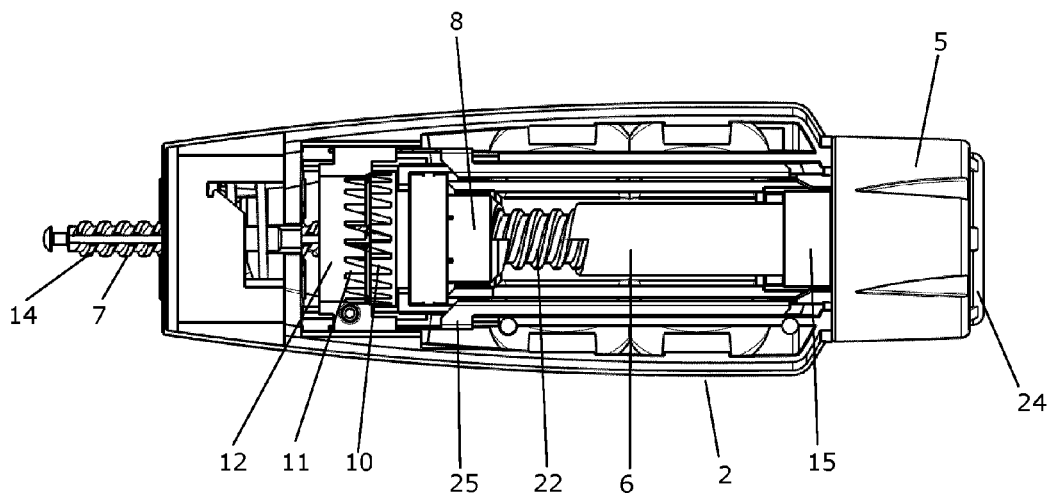

FIGS. 3a and 3b show the injection device 1 of FIGS. 1 and 2 in a position where the injection button 24 has been pushed in a distal direction as described above. In FIG. 3b it can be seen that the teeth 10, 11 have been moved out of engagement. The position of the dosage tube 6 is the same as in FIG. 2, i.e. the injection device 1 has not yet started injecting the set dose.

The compressed spring 19 pushes against the dosage tube 6, thereby urging it in a distal direction. Since the locking nut 8 is now allowed to rotate, the dosage tube 6 is allowed to move in a distal direction, while forcing the locking nut 8 to rotate due to the connection between the outer thread 22 of the dosage tube 6 and the inner thread 23 of the locking nut 8. The energy stored in the compressed spring 19 will cause the dosage tube 6 to perform this movement. Due to the connection between the inner thread 21 of the dosage tube 6 and the outer thread 14 of the piston rod 7, the piston rod 7 is moved along in this movement. The piston rod 7 is arranged in abutment with a piston (not shown) arranged in a cartridge. Accordingly, moving the piston rod 7 as described above causes the set dose of drug to be expelled from the injection device 1. The injection movement may be halted at any time during injection by releasing the injection button 24. The dose movement may be continued by once again pushing the injection button 24 in the distal direction.

Figure 9:
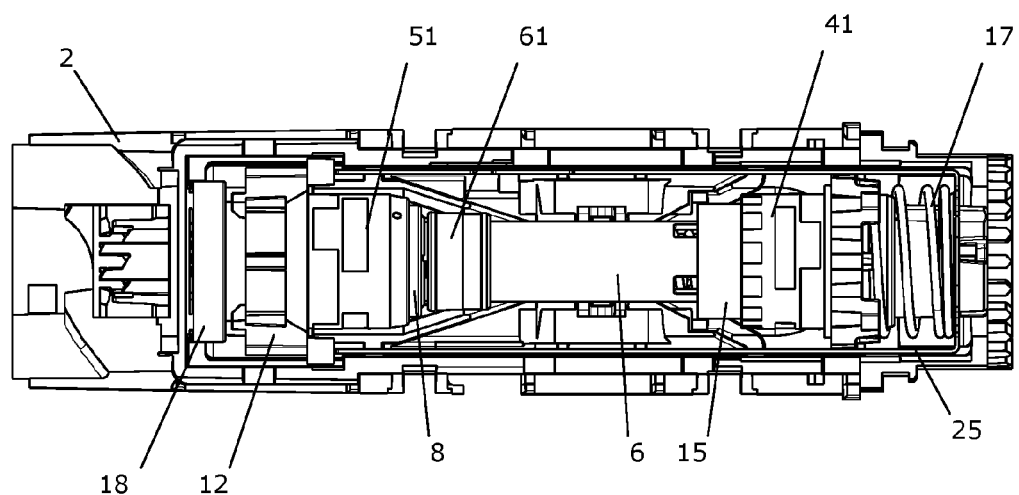
FIG. 9 is a top view of components shown in FIG. 6 and including a housing component.

In the shown embodiment, the injection button 24 is provided with a plurality of axially extending teeth (not shown) arranged to releasably engage corresponding teeth (not referenced) formed in the housing component 2 (cf. FIGS. 2a, 3a and 9). The engagement of the two sets of teeth is initiated upon pressing in of the injection button 24, and the engagement is released when the injection button 24 moves into its proximal position. Hence, manipulation of the dose knob 5 to alter a set dose during the injection movement is prevented.

Figure 4A:
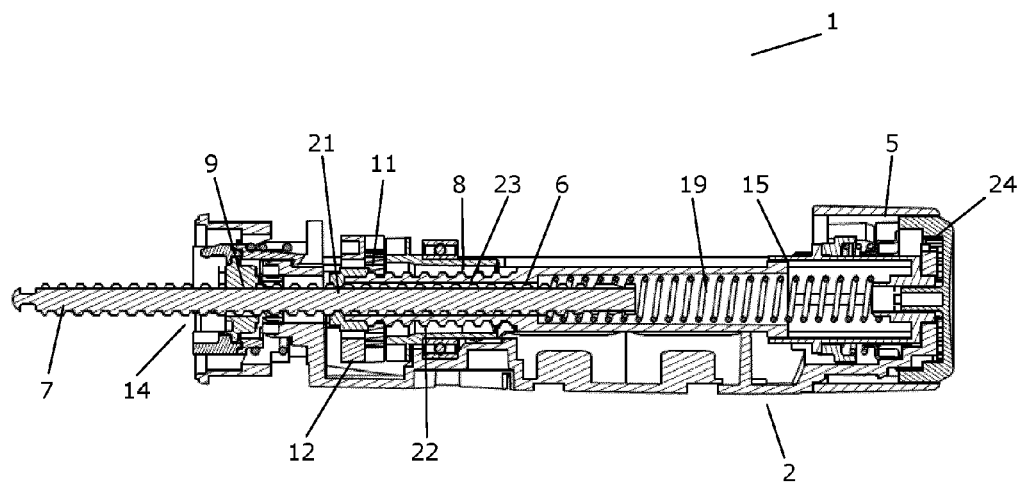
FIGS. 4a and 4b shows similar views of the injection device of FIGS. 1-3 in a position where a dose has been injected and the injection button is still pushed.
Figure 4B:
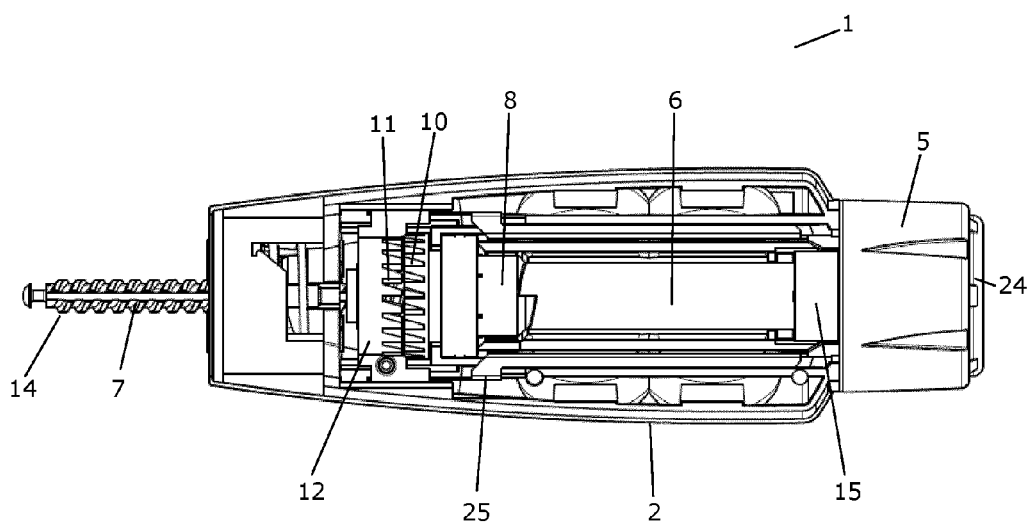

FIGS. 4a and 4b show the injection device 1 of FIGS. 1-3 in a position where injection of the set dose has been completed. Comparing FIG. 3 and FIG. 4 it can be seen that the dosage tube 6 has been returned to the position shown in FIG. 1. However, the piston rod 7 has been moved in a distal direction as compared to the position shown in FIG. 1, thereby indicating that a dose has been injected.

In accordance with the above, as the locking nut 8 only rotates during the injection process, i.e. from the start of the dosing movement of dosage tube 6 till the end of dose state is reached, the locking nut 8 performs as a dosing member for metering doses expelled from the device.

In the shown embodiment, the piston rod 7 is rotationally locked with respect to the housing component 2 during dose setting and injection operations. However, in an alternative embodiment, the piston rod 7 may be configured to rotate during the dosing movement in a manner as described in WO 2006/114395. As known in the art, the rotational lock or the rotational guiding of piston rod 7 relative to housing component 2 may be provided by means of a locking disc 9 which engages a track or thread on piston rod 7 and which is locked relative to the housing during the dose setting and dose injection process.

FIG. 5 is an exploded view of the injection device 1 of FIGS. 1-4. For the sake of clarity, only the parts necessary for explaining the operation of the injection device 1 are shown. In FIG. 5 the connecting part 25, the knurled disc 16, the click spring 17 and the ball bearing 18 are clearly visible.

Turning now to FIGS. 6 through 10 a dose setting and injection mechanism is shown which in most aspects are similar to the one of the device shown in FIGS. 1-5 but which include electronic components enabling the position detection of specific mechanical components incorporated in the device and allowing the monitoring of the mechanical components during operation of the device 1. Further, the electronic components may include an electronically controlled display and/or communication means for utilizing information relating to the detected position data, e.g. a number of set and/or expelled doses. In FIGS. 6-10, the parts that are shown which correspond to similar parts shown in FIGS. 1-5 have been provided with identical reference numerals. Likewise, only the parts necessary for explaining the operation of the electric components of the injection device 1 are shown.

Figure 6:
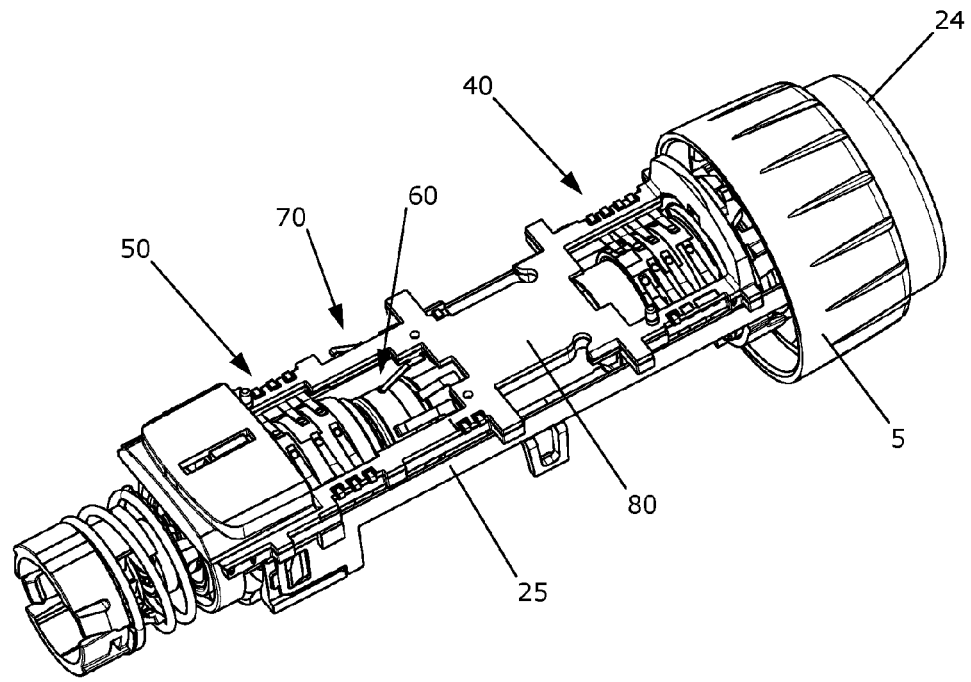
FIG. 6 is a perspective view of device similar to the device shown in FIGS. 1-5, including a first subset of sensor elements of the electronic sensing system according to the present invention.

In an exemplary embodiment and as identified in FIG. 6, four switch arrangements are provided for detecting the individual mechanical movements and states within the device mechanism. A first sensor arrangement 40 is associated with the dosage tube 6 to provide positional data relating to the rotational position of the dosage tube 6 relative to the device housing. A second sensor arrangement 50 is associated with the locking nut 8 to provide positional data relating to the rotational position of the locking nut 8 relative to the device housing. A third sensor arrangement 60, in the following referenced as Dosage Tube Sensor (DTS), is also associated with the dosage tube 6 and provides information relating to the axial position of dosage tube 6, i.e. whether the dosage tube 6 is within a predefined amount of axial travel distance from the end of dose position. Further, a fourth sensor arrangement 70 may include a switch which provides data relating to the axial position of the injection button 24, thus also the axial position of connecting part 25 and locking item 12. Hence, sensor arrangement 70 provides data as to whether the injection device 1 is in the Dose Setting Mode or in the Dosing Mode as defined above.

In the shown embodiment, the sensor arrangements 40, 50, 60 and 70 are formed as conductive switch based sensors which are coupled to an electronic control circuit incorporating a processor and being powered by a power source. In FIG. 6, a switch frame 80 is visible which is configured to hold and retain various contact elements in the form of contact arms of the sensor arrangements 40, 50, 60 and 70 in fixed relationship with the housing component 2.

The first sensor arrangement 40 used for detecting a set dose is based on a principle of detecting the rotational motion between the dosage tube 6 and the switch frame 80. As the dose setting item 15 rotates together with the dosage tube 6 and as the dose setting item 15 is mounted axially fixed in the device 1, the dose setting item 15 is utilized for detecting rotational movements during a dose setting operation. By keeping track of the rotation of dose setting item 15 it is possible to determine the dose set. The sensor arrangement 40 is implemented as a Gray code pattern (referenced first Gray code pattern 41) which is fixedly arranged relative to dose setting item 15. The first Gray code pattern 41 is formed as a cylindrical drum being swept by a set of contact arms comprised within the switch frame 80 as the dosage tube 6 is rotated. Hence, it is possible to detect direction and keep count of the net dose set. The set of contact arms are formed as a group of eight contact arms below referred to as the first group of contact arms 42.

The second sensor arrangement 50 used for detecting the amount dosed is based on the same principle utilizing a first Gray code pattern 51 provided as a cylindrical drum fixedly arranged relative to the locking nut 8. This Gray code pattern 51 is being swept by a second group of contact arms 52 which in the shown embodiment consist of six contact arms.

The first and second gray code patterns 41 and 51 are provided as galvanically conducting patterns having a series of electrically insulating fields disposed thereon. Alternatively, the first and second gray code patterns may be formed as a generally electrically insulating pattern having plurality of galvanically conducting field disposed thereon.

As for the contact elements, the state of each individual contact arm is detected by the switch sensor interface of the electronic control circuit and the information is processed by an algorithm implemented in the switch sensor interface. In this way the switch sensor interface counts the amount set, counts the amount dosed, and presents the value of these counters to the processor for further processing the data.

Electrically the sensors are configured as switches connected to ground, and the corresponding inputs to the electronic control circuit are held high by pull-up resistors to ensure a well-defined signal level. An open switch will not consume any power, but a closed switch will consume power as its pull-up resistor connects supply voltage and ground. A power conservation strategy is implemented that disables the pull-up resistors for the switches that are closed in the same manner as described in WO 2010/052275.

Such sensor system will not consume power continuously, but with this strategy only transitions that results in switches being closed can be detected. A switch that opens will not generate a rising voltage on its corresponding input since the pull-up resistor for that input has been disabled.

Figure 7:
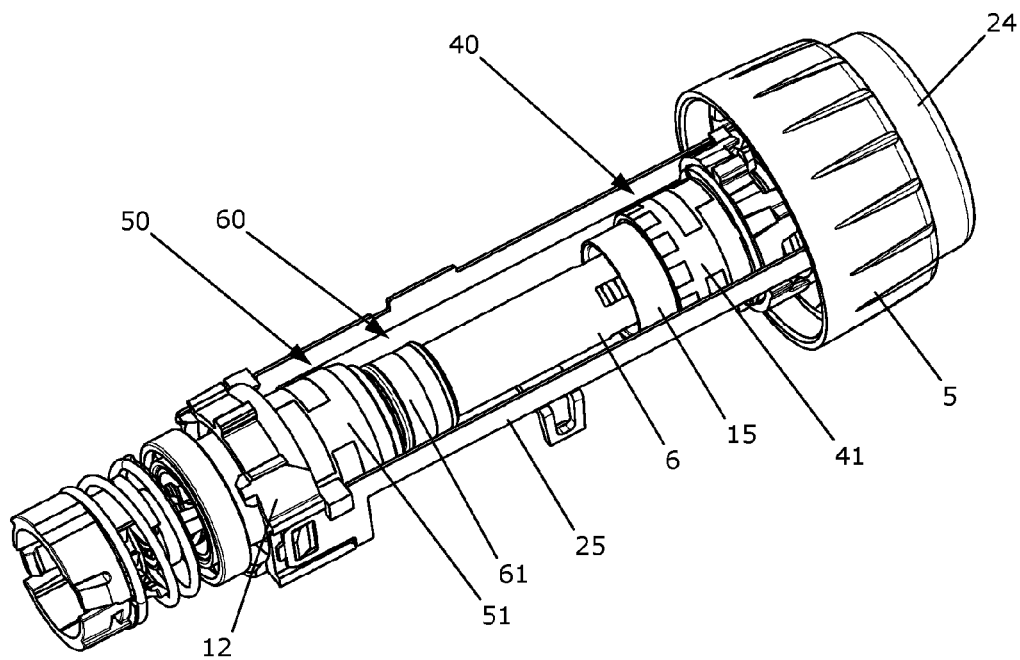
FIG. 7 is a perspective view similar to FIG. 6 and including first and second subsets of sensor elements of the electronic sensing system.

FIG. 7 and FIG. 9 show perspective and top views similar to the view as shown in FIG. 6 but where the switch frame 80 has been omitted to reveal the first Gray code pattern 41 and the second Gray code pattern 51.

Figure 8:
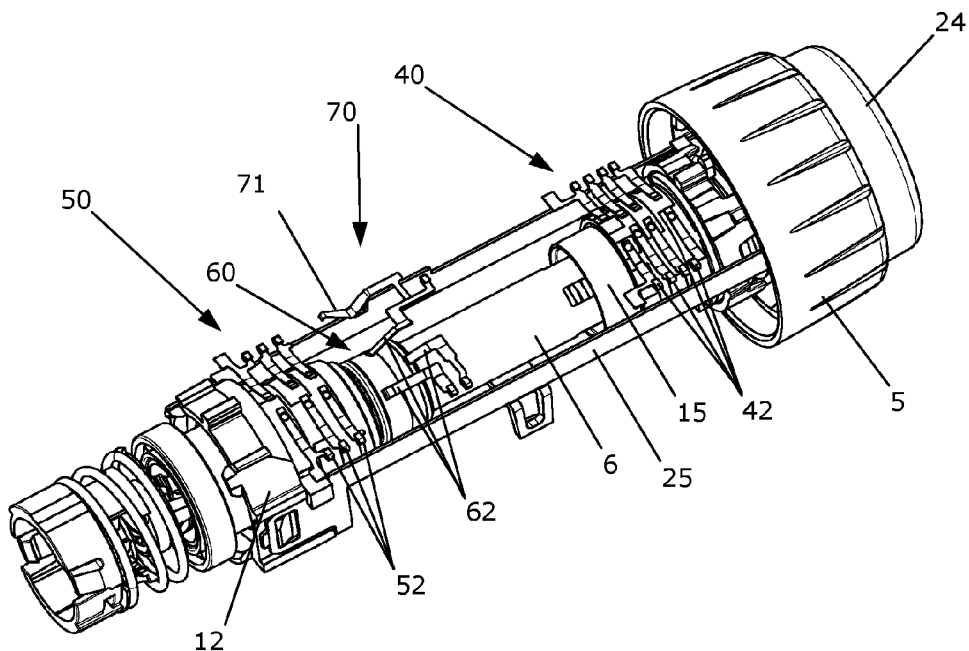
FIG. 8 is a perspective view similar to correspond to FIG. 7 and further showing a switch frame.
Figure 10:
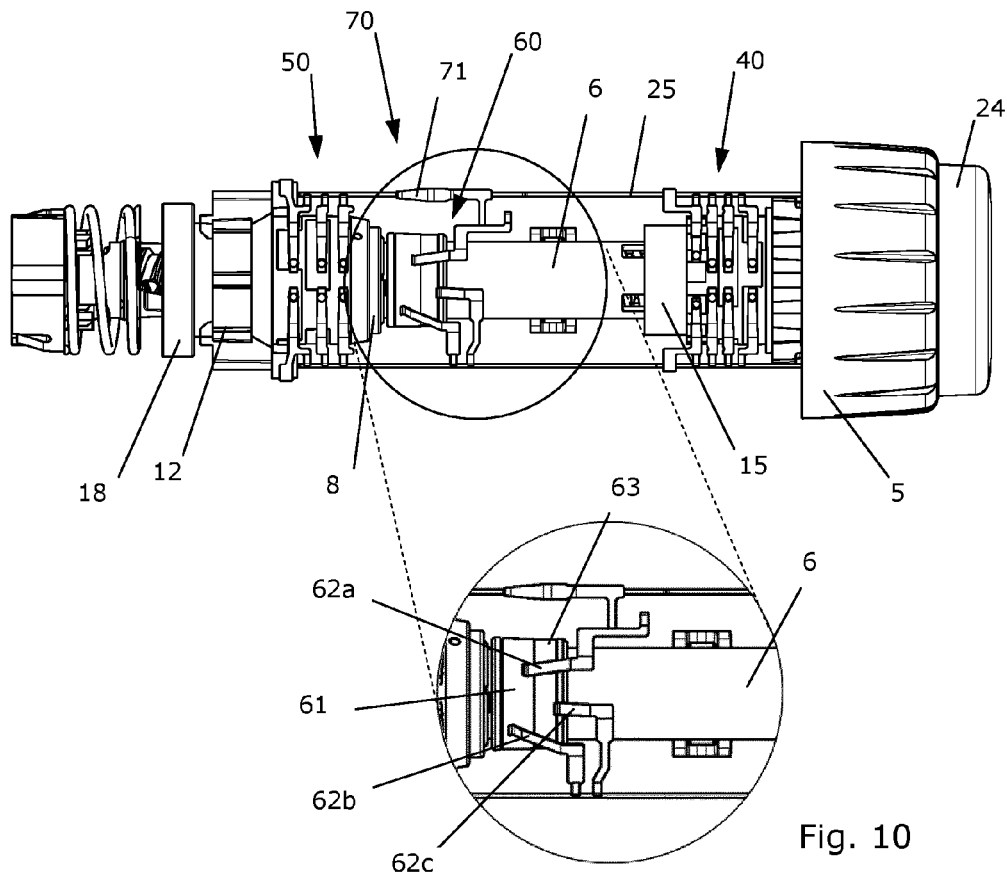
FIG. 10 is a top view corresponding to FIG. 7.

Further, FIG. 8 and FIG. 10 show similar perspective and top views where the contact arms of the switch frame 80 are visible.

Figure 11A:
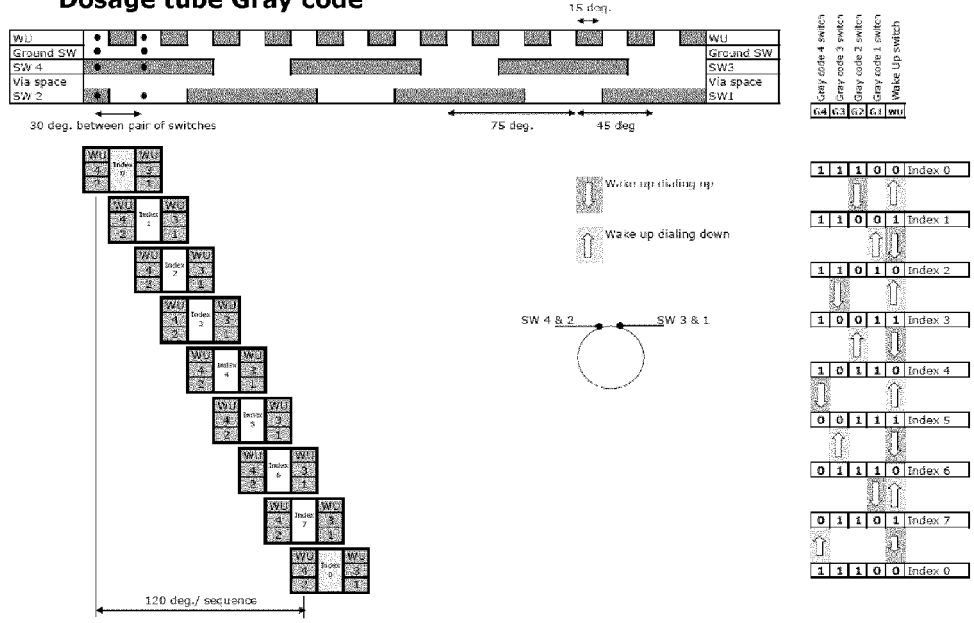
FIG. 11a shows a schematic representation of a sensor system associated with a dosage tube.
Figure 11B:
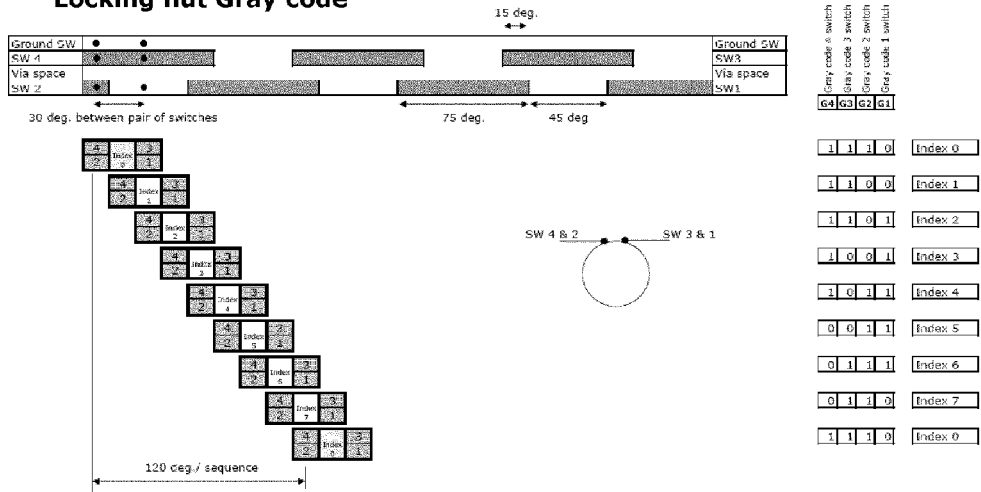
FIG. 11b shows a schematic representation of a sensor system associated with a locking nut.

The first Gray code pattern 41 is schematically represented in FIG. 11*a* and the second Gray code pattern 51 is schematically represented in FIG. 11*b*. The Gray code patterns 41 and 51 are based on a click mechanism associated with the dose setting item wherein 24 rotational steps are provided for each full revolution of dose knob 5 relative to the housing component 2. In this embodiment, the Gray code patterns have a rotational resolution corresponding to the dose increments defined by the click-mechanism, i.e. a pattern which changes state every 15 deg. angle of rotation. In other embodiments, the resolution of the Gray code patterns may be provided as two or three times the resolution defined by the click mechanism.

The first and second Gray code patterns have a code length of 8 codes (Index 0 through Index 7) and are each disposed within a 120 deg. span pr. sequence. Hence, for each full revolution that the dose setting item 15 and locking nut 8 undergoes, the contact arms will swipe the respective Gray codes three times.

Each of the first and second Gray code patterns comprises separate tracks formed as a number of circular bands. A first circular band defines a continuous electrically conducting ground pattern (designated Ground SW). A set of two contact arms provides for redundant galvanic coupling to the first circular band of the Gray code patterns. The Gray code patterns further comprises two circular patterned bands each defining generally isolating fields of angular width 75 deg. spaced apart by 45 deg. conductive traces. The first of the two circular patterned bands is offset by an angle of 15 deg relative to the other of the two circular patterned bands. Contact arms designated SW 1, SW 2 are arranged to cooperate with the first circular patterned bands and contact arms designated SW 3 and SW 4 are arranged to cooperate with the other. The contact arms SW 1 and SW 2 are positioned 30 deg. apart. Also the contact arms SW 3 and SW 4 are positioned 30 deg. apart.

The first Gray code pattern further includes a further track forming a circular band of alternating conducting and isolating fields each having an angular width of 15 deg. This circular band is provided as a first wake-up track. Also for this track a set of two contact arms spaced 30 deg. apart swipes this circular band and provides for redundant electrical connection.

FIGS. 12*a* and 12*b* show table values of the first and the second sensor arrangement for each of the sequences Index 0 through Index 7 for a Gray code lay-out as shown in FIGS. 11*a* and 11*b* respectively. Both Gray code patterns provide an absolute measure of the rotational position within a sequence n of 8 rotational positions.

As noted above, a switch that opens will not generate a rising voltage on its corresponding input since the pull-up resistor for the input has been disabled. Hence, having a Gray code pattern as defined in FIGS. 11b and 12b only the transitions 0-1, 2-3, 4-5 and 6-7 can be detected when rotating that particular Gray code pattern clockwise, and 0-7, 2-1, 4-3 and 6-5 can be detected when rotating counter-clockwise. Hence, by means of the first wake-up track referred to above it is ensured that the pull-up resistors are enabled when needed. Referring to the table shown in FIG. 12a, for the first Gray code pattern 41 shown in FIG. 11a, it is noted that there will always be a switch that closes when going from an index to its neighbour index in either rotational direction. Hence a detectable level will always occur.

Other embodiments may include a second wake-up track (not shown) configured to be sensed by a set of contact arms. The second wake-up track likewise forms a circular band of alternating conducting and isolating fields where the fields of the second wake up track are inverted relative to the fields of the first wake-up track. The second wake-up track enables wake-up in the presence of a single failing Gray code switch arm.

For the second Gray code pattern 51 which is associated with the locking nut 8 another implementation is chosen. Here all pull-up resistors are enabled when ever the fourth sensor arrangement 70 detects that the injection button 24 is pressed in; and deactivated when the fourth sensor arrangement 70 detects that the injection button is in its non-depressed state. In this way the second sensor arrangement 50 associated with the locking nut 8 and relating to dosing is only consuming power when the device 1 is actually in Dosing Mode.

As noted above, the third sensor arrangement 60 provides information as to whether the dosage tube 6 is within a predefined axial distance from the position the dosage tube 6 assumes when positioned in the end of dose position. In one form, the third sensor arrangement 60 may be based on a simple principle of two contact arms being connected by a conductive circular band arranged fixedly relative to dosage tube 6 at a particular axial position thereof wherein the conductive circular band is provided between adjacent regions of electrically insulating material. The conductive circular band may be configured as a conductive cylinder 61 mounted or applied onto the dosage tube 6 where the surface of the neighbouring areas on each side of the conductive cylinder 61 defines electrically non-conductive areas. For example, the dosage tube 6 component may be made of an electrically non-conductive material having the conductive cylinder 61 fixedly attached. In other embodiments, a cylindrical component is attached to the dosage tube 6 where the cylindrical component includes an electrically conductive band situated between electrically non-conductive bands.

Figure 13:
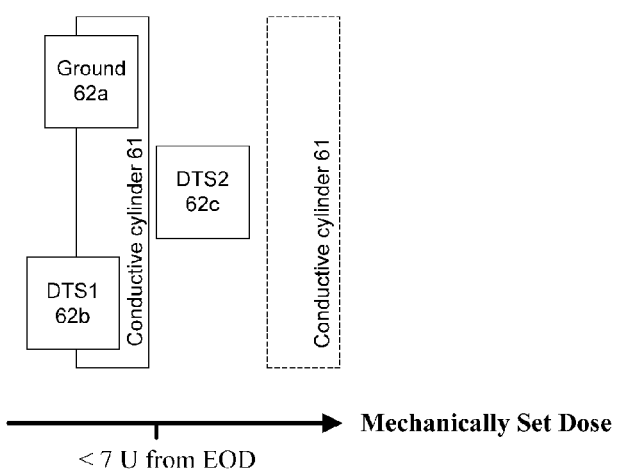
FIG. 13 is a schematic representation of an end of dose sensor arrangement.

In the shown embodiment, as shown in FIG. 10, the third sensor arrangement 60 is provided as three contact arms 62 (62a, 62b and 62c) that each are adapted to engage the conductive cylinder 61 for particular positions that dosage tube 6 is adapted to assume. The three contact arms 62a, 62b and 62c are mutually separated along the axial direction. In the shown embodiment, the first contact arm 62a is connected to ground whereas each of the contact arms 62b and 62c is provided as an electrode that is held high by a pull-up resistor. Reference is made to FIG. 13 that shows a schematic representation of the third sensor arrangement 60, wherein the rectangular box provided with full lines represents conductive cylinder 61 shown at a location close to the end of dose position. Further, FIG. 13 shows the contact arms "Ground" 62a, "DTS1" 62b and "DTS2" 62c, where references DTS1 and DTS2 respectively refer to Dosage Tube Sensor 1 (DTS1) and Dosage Tube Sensor 2 (DTS2). In addition, the rectangular box provided by dashed lines represents the conductive cylinder 61 in a position corresponding to a particular dose setting where the dosage tube 6 is located further away from the end of dose state.

When the conductive cylinder 61 is not in the proximity of its end of dose position, e.g. further away than p index positions, such as 6 index positions, from the end of dose position, the conductive cylinder 61 will not provide a galvanically connection between the two contact arms 62a and 62b and consequently the switch referenced DTS1 which associates with contact arm 62b will be in an open state. When the dosage tube 6 reaches a point in the proximity of its end of dose position (an arbitrary point that is within 0-6 index positions from the end of dose position), the conductive cylinder 61 will connect the contact arms 62a and 62b and cause the DTS1 sensor arrangement to shift into a closed state.

It is to be noted that in other configurations the switch DTS1 included in sensor arrangement 60 may be configured to enable a switching from the open state into the closed state at other locations. Also, the shift pattern may be the inverse to that described in connection with the depicted embodiment. Typically, the location of the switching point for DTS1 will be selected in the upper range of the code length n of the Gray code patterns. For example for a code length of n=8 codes, the location p for the switching point may be selected at index 4, 5 or 6 index locations from the end of dose state.

In addition and as apparent from FIGS. 10 and 13, a third contact arm 62c is configured to engage the conductive cylinder 61 for a particular range of relative axial positions between dosage tube 6 and locking nut 8 and thus constitutes a further switch DTS2. However, as schematically depicted in FIG. 13, contact arm 62c is located axially spaced away from the contact arm 62b so that the contact arm 62c will not be engaging the conductive cylinder band 61 when the device is in the end of dose state. When the conductive cylinder 61 connects the contact arms 62a and 62c the switch referenced DTS2 which associates with contact arm 62c will be in a closed state. When conductive cylinder 61 does not connect both contact arms 62a and 62c the DTS2 switch will be in an open state.

The different locations for the transition points associated with the two switches DTS1 and DTS2 are utilized to detect eventual liquid ingress into the interior of the device such as liquid drug that may leak from a held cartridge or liquid from external sources that may cause to enter into the housing of the device. The control circuit of the device is configured to be able to distinguish between a connection caused by the conductive cylinder (DTS1 and Ground connected) and a short circuit (DTS1, DTS2 and Ground connected), e.g. caused by liquid drug ingress.

During operation of the device, depending on the actual axial locations of the contact arms 62b and 62c, and the position and geometry of the conductive cylinder 61, for each position that dosage tube 6 will assume there will be a predefined pattern of output signals from the respective switches DTS1 and DTS2. Hence for a safely working device where no liquid is present at the sensor arrangement 60 a predefined pattern of signals will be obtainable from each of the sensors DTS1 and DTS2. The processor is configured to detect the state of the signals from DTS1 and DTS2 and to analyse the signals taking into consideration the instantaneous determined position of the dosage setting, i.e. based on the signals from the sensor arrangements 40 and 50. Should the output signals from the switches DTS1 and DTS2 for a particular axial position of the dosage tube 6 indicate that liquid is present at or around any of the contact arms 62a, 62b and 62c the device will provide a warning indication, The contact arms 62a, 62b and 62c and the conductive cylinder 61 may be so configured that for a particular dosage setting or a range of dosage settings, both switches DTS1 and DTS2 will simultaneously be in a closed state. In other configurations, the switches DTS1 and DTS2 will not be closed at the same time irrespective of the dosage setting meaning that the switches DTS1 and DTS2 will have no overlap.

The fourth sensor arrangement 70 is based on a switch being closed. In the depicted embodiment a contact arm 72 is manipulated by a flange (not shown) on the connecting part 25. When the injection button is not activated (not pushed in) the flange will not activate the switch and consequently the switch will remain in an open state. When the injection button 24 is pushed in, the flange will perform an axial movement and cause the fourth sensor arrangement 70 to enter a closed state. Electrically the sensor is configured as a switch connected to ground, and the corresponding input to the electronic control circuit is held high by a pull-up resistor to ensure a well-defined signal level.

The mechanical coupling between the dosage tube 6 and the locking nut 8 during dose setting (dialling up and dialling down) as well as during dosing means that the first and second Gray code patterns 41 and 51 will always end up at the same relative rotational position after a complete dosing has taken place. Hence, in the end of dose state of the device 1, the index of the first Gray code pattern 41 will be the same as the index of the second Gray code pattern 51 provided that the two Gray code patterns during manufacture have been aligned corresponding to an alignment in the end of dose state of the device 1.

As noted above, the dose setting mechanism may be designed to cover a dosable range that may be chosen as 80 or 100 index positions. Due to this and due to the fact that the shown embodiment utilizes Gray code patterns which only provide an absolute detection of the rotational position within a sequence of 8 rotational positions (corresponding to 120 deg. of rotation) the monitoring during operation of the device 1 is based on counting the number of full sequences as well as fractional sequences of rotation performed during relative rotational movement between the dosage tube 6 and the locking nut 8. Hence, there will be a multitude of relative rotational positions between dosage tube 6 and locking nut 8 where the signals from the first and second sensor arrangements are the same. Likewise, there will be a plurality of relative rotational positions between dosage tube 6 and locking nut 8 which correspond to the relative rotational position at the end of dose state of the device 1. Therefore, the synchronization between the first and the second sensor arrangements are being monitored.

In the above sensor configuration, the exact adjusted dose size and/or the total amount of an expelled dose will not be detectable when basing the monitoring solely on instantaneous data provided by the first sensor arrangement 40 and the second sensor arrangement 50. Should one or more interrupts be missed during operation of the device there will be a risk that the synchronization between the electronic sensor system and the mechanical system may fail.

In order to ensure synchronization between the mechanical system and the electronic system, the information provided by the third sensor arrangement 60 is utilized which provides a detection that the relative rotation between dosage tube 6 and locking nut 8 is within 1 sequence (such as within 0-7 Index positions or alternatively 0-6 index positions) from the end of dose state. Combining this information and the differential information from the first sensor arrangement 40 and the second sensor arrangement 50 a detection of the exact end of dose state can be accurately determined. If a discrepancy should occur between the continuous monitoring and instantaneous information obtained from the sensor arrangements 40, 50, 60 and 70, the electronic control circuit will detect this as a failure and provide a warning indication to the user of the device. If the error is one of a recoverable kind, the device may be reset by means of the signals from the first sensor arrangement 40, the second sensor arrangement 50 and the third sensor arrangement 60 and the synchronization between the mechanical system and the electronic system may be recovered. If the error is irrecoverable, a warning as to this instance may be indicated to the user.

Due to the rotational stop surfaces of the dosage tube 6 relative to the locking nut 8 at the end of dose state, the relative position are well defined and thus allows the device to reset itself during normal operation, e.g. during operation of the injection button 24 and/or the dose knob 5. Hence, the device may be so adapted that the first and the second sensor arrangements synchronize automatically when the device is in the end of dose state.

The above described sensor values are used for estimating the dose as set and the dose as expelled so as to provide an indication on a display of the device (not shown). In the shown embodiment, during a dosing operation, the display may be configured to continuously show the part of a set dose that remains to be injected, e.g. as defined by the display refresh rate.

The electronic control circuit of the injection device 1 may further include a memory circuit adapted to hold information relating to a plurality of set and/or injected doses and the timing information relating to each such dose. Hereby the dosing history may be browsed through for example by utilizing the injection button 24 as a means for stepping through the injection history.

The electronic control circuit of the injection device 1 may in addition, or as an alternative, be provided with means for communicating the contents of the memory to an external apparatus, such as a personal computer, a mobile communication terminal such as a SmartPhone or such as a glucose meter (BGM/CGM). Such means for communication may be provided by means of an optical port such as an IR port, an RF communication antenna such as for communicating via Bluetooth or NFC, or via cable connection, etc.

It is to be noted that the dose setting and injection mechanism described above only relates to one particular embodiment according to the invention. Other dose setting and injecting mechanisms may be utilized in accordance with the present invention such as the dose setting and injection mechanism incorporated in the device shown in FIGS. 1-7 of WO 2007/134954, which relates to a device where the user of the device manually drives forward a piston rod during expelling of a set dose.

The invention claimed is:

1. An injection device for setting and expelling set doses of a drug from a drug-filled cartridge, the cartridge comprising an outlet and a slideably arranged piston which is driveable in a distal direction to expel the drug through the outlet, the injection device comprising:
   a housing,
   a piston rod adapted to cooperate with the piston of the cartridge to cause a set dose to be expelled,
   a dosing member mounted rotatably movable but axially fixed in the housing, the dosing member being prevented from rotating during dose setting and allowed to rotate during dose delivery, the dosing member comprising a first thread, a driver coupled to the piston rod, the driver comprising a second thread engaged with the first thread of the rotatable dosing member, wherein the driver moves in a proximal direction during dose setting as it rotates through the engagement with the dosing member away from an initial rotational position relative to the dosing member, and wherein the driver performs a non-rotational displacement in the distal direction during dose delivery while the dosing member rotates, a first sensor associated with the driver and adapted to provide data indicative of the rotational position of the driver relative to the housing, a second sensor associated with the dosing member and adapted to provide data indicative of the rotational position of the dosing member relative to the housing, a third sensor associated with the driver and adapted to provide data indicative of the axial position of the driver relative to the housing, and a control circuit coupled to the first, second and third sensors, the control circuit being adapted to determine the rotational positions of the driver and the dosing member and adapted to determine an amount of a set dose and/or an amount of an expelled dose based on the rotational position of the driver relative to the rotational position of the dosing member, wherein the control circuit is adapted to determine the state wherein the driver is in the initial rotational position relative to the dosing member based on data from the first sensor, data from the second sensor and data from the third sensor.

2. An injection device as in claim 1, wherein the driver is rotatable relative to the dosing member through an angular movement exceeding one revolution.

3. An injection device as in claim 1, wherein the driver is rotatable relative to the dosing member in discrete rotational steps by means of a click mechanism.

4. An injection device as in claim 1, wherein the first and/or the second sensor is/are adapted to provide rotational position data corresponding to N discrete rotational steps distributed evenly over 360 degrees of rotation.

5. An injection device as in claim 1, wherein the first and/or the second sensor is/are adapted to provide unique rotational position data for each respective rotational positions of the respective one of the driver and the dosing member over a range of n rotational positions, wherein n is a division of N and N/n is a natural number.

6. An injection device as in claim 5, wherein the third sensor and the control circuit are adapted to determine whether or not the driver is in the range of p rotational positions from said initial rotational position of the driver relative to the dosing member, p being a number selected from the range from 0 to 7.

7. An injection device as in claim 1, wherein the control circuit is adapted to count the amount of a set dose and/or the amount of an expelled dose based on the number of complete and fractional relative rotations between the driver and the dosing member.

8. An injection device as in claim 1, wherein the initial rotational position of the driver relative to the dosing member is determined by means of the third sensor and by means of the differential rotational position between the driver and the dosing member as determined by the first sensor and the second sensor.

9. An injection device as in claim 1, wherein the third sensor is adapted to provide an output signal, when the driver is within p rotational positions from said initial rotational position of the driver relative to the dosing member.

10. An injection device as in claim 1, wherein the third sensor adapted to provide one or more state changes only when the driver is within p rotational positions from said initial rotational position of the driver relative to the dosing member.

11. An injection device as in claim 1, wherein the first and/or the second sensor comprises one or more code tracks arranged as circumferential band(s) on a cylindrical surface, either on an interior cylindrical surface or an external cylindrical surface.

* * * * *